United States Patent [19]

Ramey et al.

[11] Patent Number: 5,493,922
[45] Date of Patent: Feb. 27, 1996

[54] LIQUID LEVEL SENSING PROBE AND CONTROL CIRCUIT

[75] Inventors: B. Edward Ramey; Mario Moreno, both of Durham, N.C.

[73] Assignee: Akzo N.V., Velperweg, Netherlands

[21] Appl. No.: 88,656

[22] Filed: Jul. 9, 1993

[51] Int. Cl.$^6$ ............................ G01F 23/26; G05D 9/12; G01N 35/10; G01N 1/10
[52] U.S. Cl. ...................... 73/863.02; 73/863.01; 73/863.11; 73/863.85; 73/864.25; 73/304 C; 340/620; 137/392
[58] Field of Search .................... 340/620; 137/392; 73/863.11, 863.01, 863.85, 864.74, 864.73, 864.24, 864.25, 864.23, 304 R, 304 C, 863.02, 863.03

[56] References Cited

U.S. PATENT DOCUMENTS

| | | | |
|---|---|---|---|
| 4,173,893 | 11/1979 | Hedrick | 340/620 X |
| 4,380,091 | 4/1983 | Lively | 137/392 X |
| 4,559,507 | 12/1985 | Ramsdale et al. | 73/304 C X |
| 4,736,638 | 4/1988 | Okawa et al. | 73/864.24 |
| 4,912,976 | 4/1990 | Labriola, II | 73/290 R |
| 4,943,353 | 7/1990 | Shannon | 137/392 X |
| 5,049,826 | 9/1991 | Sasao | 73/864.24 X |
| 5,130,254 | 7/1992 | Collier et al. | 73/863.01 X |
| 5,178,019 | 1/1993 | Keiter | 73/864.24 X |
| 5,216,926 | 6/1993 | Lipsom | 73/863.01 X |
| 5,275,951 | 1/1994 | Chow et al. | 73/864.24 X |
| 5,365,783 | 11/1994 | Zweifel | 73/304 C |

OTHER PUBLICATIONS

Cavro Liquid Level Sensors Specification Sheet, Cavro Scientific Instruments, Inc., Sunnyvale, CA published by Jun. 1993 6 pages.
Hamilton M/L 2200 Liquid Handling System Specification Sheet ZC-0006, Oct. 1988 3 pages.
"Security-Circuit Cookbook", R. Marston, Radio-Electronics, Jul. 1990, pp. 56-60.
National Semiconductor brochure; LM 1830 Fluid Detector; pp. 5-123—pp. 5-126; published by Jan. 1995.

Primary Examiner—Thomas P. Noland
Attorney, Agent, or Firm—Gregory R. Muir; William M. Blackstone

[57] ABSTRACT

A method and apparatus for a liquid level sensor control circuit of a bioassay apparatus for controlling a position of a sampling probe with respect to a surface of a liquid in a container. The apparatus includes a sampling probe, an oscillator circuit coupled to the sampling probe for producing a first output signal having a constant frequency, a comparator coupled to the oscillator circuit for comparing the amplitude of the first output signal to a first reference amplitude and for producing a change signal when the amplitude of the first output signal changes with respect to the reference amplitude, and a controller responsive to the change signal for controlling the position of the sampling probe with respect to the surface of the liquid.

19 Claims, 4 Drawing Sheets

LIQUID LEVEL SENSING PROBE AND CONTROL CIRCUIT

BACKGROUND OF THE INVENTION

1. Field of the Invention

The present invention relates to a method and apparatus for detecting a surface of a liquid in a container and, more particularly, to a method and apparatus for use in an automated blood/plasma sampling system for detecting a surface of a liquid in a container and for controlling a position of a probe with respect to the surface of the liquid.

An example of an automated blood/plasma sampling system for which the present invention is applicable is disclosed, for example, in U. S. patent application Ser. No. 07/833,951 to Hulette et al., filed Feb. 11, 1992, now abandoned, which is a continuation-in-part application of U.S. patent application Ser. No. 07/443,951, filed Dec. 1, 1989, now abandoned. The subject matter of the continuation-in-part application to Hulette et al. is incorporated herein by reference. An example of a piercing and sampling probe is disclosed in U.S. patent application Ser. No. 07/874,371 filed Apr. 27, 1992, and now U.S. Pat. No. 5,354,537 by Moreno. The subject matter of the application to Moreno is incorporated herein by reference. Another example of a sampling probe is disclosed in U.S. Pat. No. 5,178,019, issued Jan. 12, 1993, to Keiter. The subject matter of the patent to Keiter is incorporated by reference herein. An example of a memory control device associated with a robotic arm controller is disclosed in a U.S. patent application Ser. No. 08/088,550 to Ramey filed concurrently with the present application and and now abandoned but continued as application Ser. No. 08/404,121 filed Mar. 14, 1995. The subject matter of the application to Ramey is incorporated by reference herein. The subject matter of the applications to Hulette et al., to Moreno and to Ramey, and the patent to Keiter are each assigned to the same assignee as the present application.

2. Description of the Related Art

Automated sample handling systems are known which automatically dispense fluid samples, such as blood plasma and reagents, into a reaction well of a cuvette. Such instruments are useful in the field of biochemical analysis for measuring blood clotting times and for automatically carrying out other bioassays. Additionally, these instruments are useful in the field of chemical assays for automatically carrying out chemical assays. An automated sample handling system for carrying out blood and plasma bioassays is described in U.S. patent application Ser. No. 07/443,951 to Hulette et al.

In this particular system, fluid samples, such as blood or plasma, are stored in containers, such as test tubes, which are vacuum sealed by way of a rubber septum that must be pierced in order to withdraw a measured amount of the sample for testing purposes. U.S. patent application Ser. No. 07/874,371 to Moreno, incorporated herein by reference, discloses an example of a piercing and sampling probe suitable for piercing and sampling a measured amount of liquid.

The Hulette et al. system also includes a temperature controlled housing provided for storing fluid samples and reagents at a relatively cool temperature for preventing degradation of the samples and reagents prior to sample analysis. The temperature controlled housing typically maintains the fluid samples and reagents at a temperature of 10° C. The actual analyses are generally carried out at 37° C. (98.6° F.), standard human body temperature. Accordingly, it is necessary to heat the fluid sample and reagents to 37° C. prior to analysis. U.S. Pat. No. 5,179,019 to Keiter, incorporated herein by reference, discloses a sample probe device useful for heating fluid samples and reagents prior to analysis.

The piercing and sampling probes in the Hulette et al. system are raised and lowered in operation by a robotic arm which maneuvers a probe between reagent containers and a reaction cuvette for automatically aspirating and dispensing reagents. The surface of a liquid, whether a sample or reagent, is detected for accurately controlling movement of the probe. Basically, the surface of the liquid is detected by detecting a change in capacitance of the probe with respect to the chassis of the automated blood/plasma sampling system.

Presently available liquid surface sensing devices supplied by CAVRO Scientific Instruments, Inc., Sunnyvale Calif., do not accurately sense small volumes of liquid while at the same time being of such small size for readily mounting on a movable rack assembly holding a sampling probe. A high sensitivity CAVRO liquid surface sensing device can detect 10 µl of a 1:10,000 dilution of normal saline when tested in a 10×75 mm glass tube. Another liquid level sensing device manufactured by Hamilton, Reno, Nev., also does not accurately sense small volumes of liquid while having a size which lends itself to mounting on a movable rack assembly holding a sampling probe. The present invention reliably senses the surface of a small volume of liquid, for example, liquid volumes less than 300 µl of saline in a plastic 3 ml reagent bottle, even while piercing a sealing septum.

SUMMARY OF THE INVENTION

The present invention accurately senses a surface of a liquid when a probe, such as a piercing or sampling probe, for a bioassay apparatus touches the surface of the liquid.

The above and other objects of the invention are accomplished by the provision of a liquid level sensor control circuit for a bioassay apparatus for controlling a position of a sampling probe with respect to a surface of a liquid in a container includes a sampling probe for touching the surface of the liquid in the container, an oscillator circuit coupled to the sampling probe for producing a first output signal having a constant frequency, where an amplitude of the first output signal changes when the sampling probe touches the surface of the liquid, a comparator coupled to the oscillator circuit for comparing the amplitude of the first output signal to a first reference amplitude and for producing a change signal when the amplitude of the first output signal changes with respect to the reference amplitude, and a controller responsive to the change signal for controlling the position of the sampling probe with respect to the surface of the liquid.

According to another aspect, a liquid level sensor control circuit for a bioassay apparatus according to the present invention also includes a rectifier coupled to the first output signal for producing a rectified output signal related to the first output signal, where the comparator compares an amplitude of the rectified output signal to the first reference amplitude for producing the change signal.

The sampling probe of the present invention can be a piercing sampling probe for sampling a liquid in a sealed container and can include a heater for heating sampled liquids. Further, the oscillator circuit and the comparator can be attached to a rack assembly holding the sampling probe.

According to another aspect of the present invention, a liquid level sensor control circuit for controlling a position of a sampling probe with respect to a surface of a liquid includes an oscillator coupled to the sampling probe for generating a constant frequency output signal having a first amplitude when the sampling probe is not touching the surface of the liquid, and having a second amplitude different from the first amplitude when the sampling probe touches the surface of the liquid, a rectifier circuit coupled to the oscillator for producing a rectified output of the constant frequency output signal, a filter coupled to the rectified output for producing a filtered signal, a detector circuit coupled to the filter for detecting when the amplitude of the constant frequency signal changes from the first amplitude to the second amplitude and generating a change signal in response, and a controller circuit responsive to the change signal for controlling the position of the sampling probe with respect to the surface of the liquid. The liquid level sensor control circuit can also include a gain control circuit coupled to the output of the rectifier for controlling a gain of the oscillator and an amplifier for amplifying the rectified output of the constant frequency output signal.

According to yet another aspect of the present invention, a method for detecting a sampling probe touching a surface of a liquid includes the steps of generating a constant frequency oscillation signal having a first amplitude when the sampling probe does not touch the surface of the liquid and having a second amplitude when the sampling probe touches the surface of the liquid, rectifying the output of the constant frequency output signal, the rectified output having a third amplitude when the amplitude of the constant frequency signal is the first amplitude and a fourth amplitude when the amplitude of the constant frequency signal is the second amplitude, detecting when the amplitude of the rectified output of the constant frequency signal changes from the third amplitude to the fourth amplitude, generating a change signal in response detecting a change from the third amplitude to the fourth amplitude indicating that the sampling probe is touching the surface of the liquid.

The method according to the present invention can further include a step of controlling a position of the sampling probe with respect to the surface of the liquid in response to the change signal and a step of adjusting the second amplitude of the constant frequency signal back to the first amplitude when detecting the amplitude of the rectified output of the constant frequency signal changes from the third amplitude to the fourth amplitude.

BRIEF DESCRIPTION OF THE DRAWINGS

A preferred embodiment of the invention will be described in conjunction with the accompanying drawings, wherein.

DETAILED DESCRIPTION OF THE INVENTION

Figure 1:
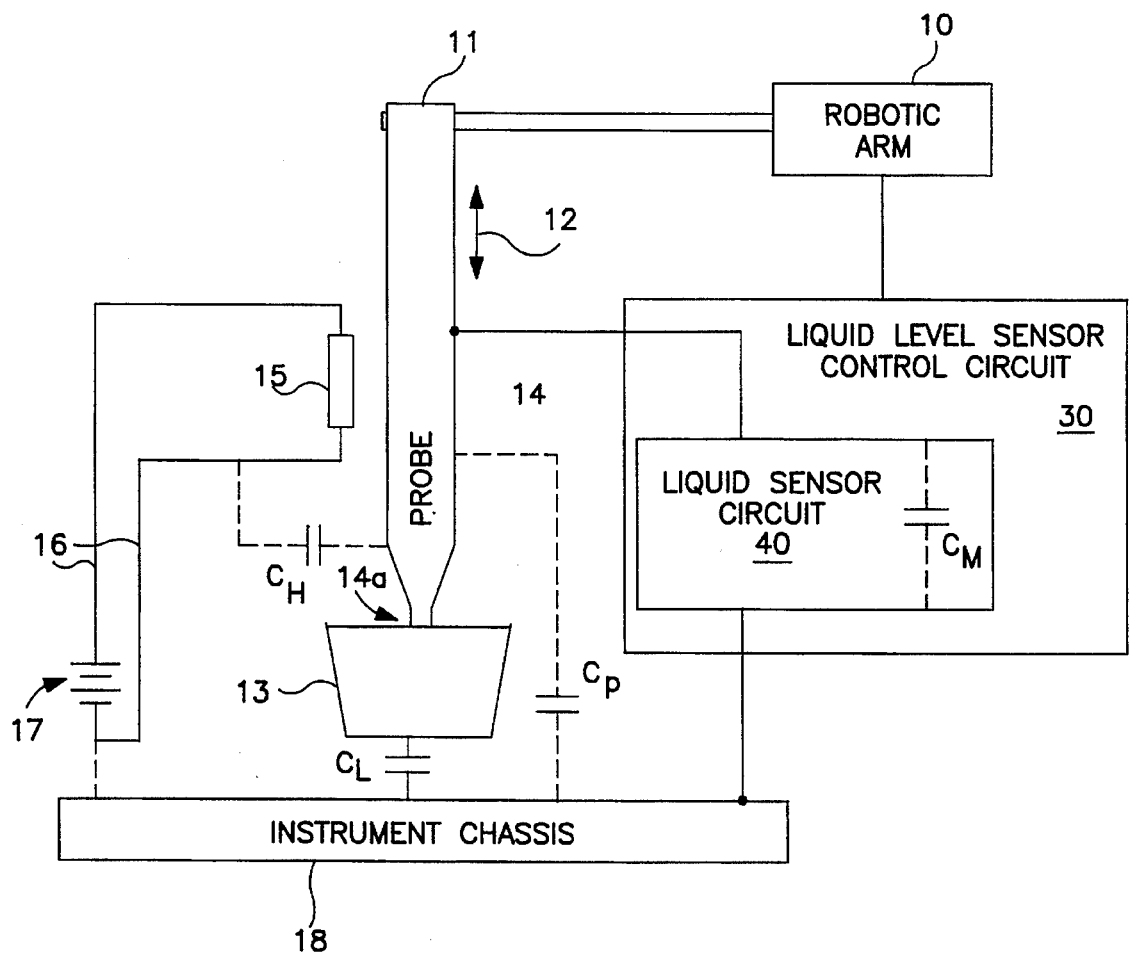
FIG. 1 is a schematic block diagram of an embodiment of a probe and a liquid sensor control circuit according to the present invention.

FIG. 1 shows a schematic block diagram of an embodiment of a probe for an automated blood/plasma sampling system and its relation to a liquid sensor circuit and control circuit according to the present invention. Robotic arm 10 maneuvers probe 11 between reagent containers, such as reservoir 13, to a reaction cuvette (not shown) for automatically aspirating and dispensing reagents as described, for example, in U.S. patent application Ser. No. 07/443,951 to Hulette et al. Robotic arm 10 raises and lowers probe 11 along the directions indicated by arrow 12 for taking a measured volume of liquid from liquid reservoir 13 or dispensing it to a reaction cuvette. Generally, probe 11 includes a metallic tube 14 having a narrow tip 14a for dipping into reservoir 13 and aspirating a measured amount of reagent. Probe 11 may also be adapted for piercing container sealed by a rubber septum to aspirate a measured volume of liquid from the container by including a pointed tip.

As previously mentioned, it is desirable in certain applications to heat the reagent in probe 11 while the probe is moved by robotic arm 10 toward a cuvette where the reagent is dispensed. In these applications, probe 11 is provided with an optional heater 15. Heater 15 preferably includes a coiled nichrome wire wrapped around tube 14 and electrically connected by wires 16 to a power supply 17 which shares a common ground with chassis 18. Power supply 17 can be either a DC or AC power supply depending on the requirements of a particular application.

In order to aspirate a measured amount of reagent from reservoir 13, it is necessary to detect when probe 11 contacts the surface of the reagent. As previously discussed, this is typically accomplished with the use of a capacitance measuring device for detecting a change in the capacitance of tube 14 with respect to the ground plane formed by chassis 18 when tube 14 contacts the reagent in reservoir 13. Tube 14 presents a first capacitance $C_P$ with respect to chassis 18. When optional heater 15 is provided, heater 15 has a common ground with instrument chassis 18 and, therefore, is capacitively a part of chassis 18. Thus, optional heater 15 presents a second capacitance $C_H$ with respect to tube 14. Liquid reservoir 13 presents an additional capacitance $C_L$ between probe 11 and instrument chassis 18. Thus, before probe 11 touches the surface of the liquid, the total capacitance $C_{T1}$ measured by the capacitance measuring device is $$C_{T1}=C_P+C_H.$$

If an optional heater is not provided, $C_H$ equals zero and the total capacitance $C_{T1}$ is $C_P$. After probe 11 touches the surface of the liquid, the total capacitance $C_{T2}$ measured by the capacitance measuring device is $$C_{T2}=C_P+C_L+C_H.$$

Detection of the additional capacitance $C_L$ by a capacitance measuring device indicates when probe 11 contacts the liquid surface in container 13. However, the presence of capacitance $C_H$ caused by an optional heater 15 can be sufficiently large to limit the ability of the capacitance measuring device to sense a change in $C_{T1}$ by $C_L$.

The liquid sensor circuit and liquid level sensor control circuit of the present invention reliably senses changes in capacitance between the probe and the system chassis even in the presence of an optional heater. In fact, the liquid level sensor system according to the present invention reliably senses the surface of, for example, liquid volumes less than 300 μl of saline in a plastic 3 ml reagent bottle, even while piercing a sealing septum.

Figure 2:
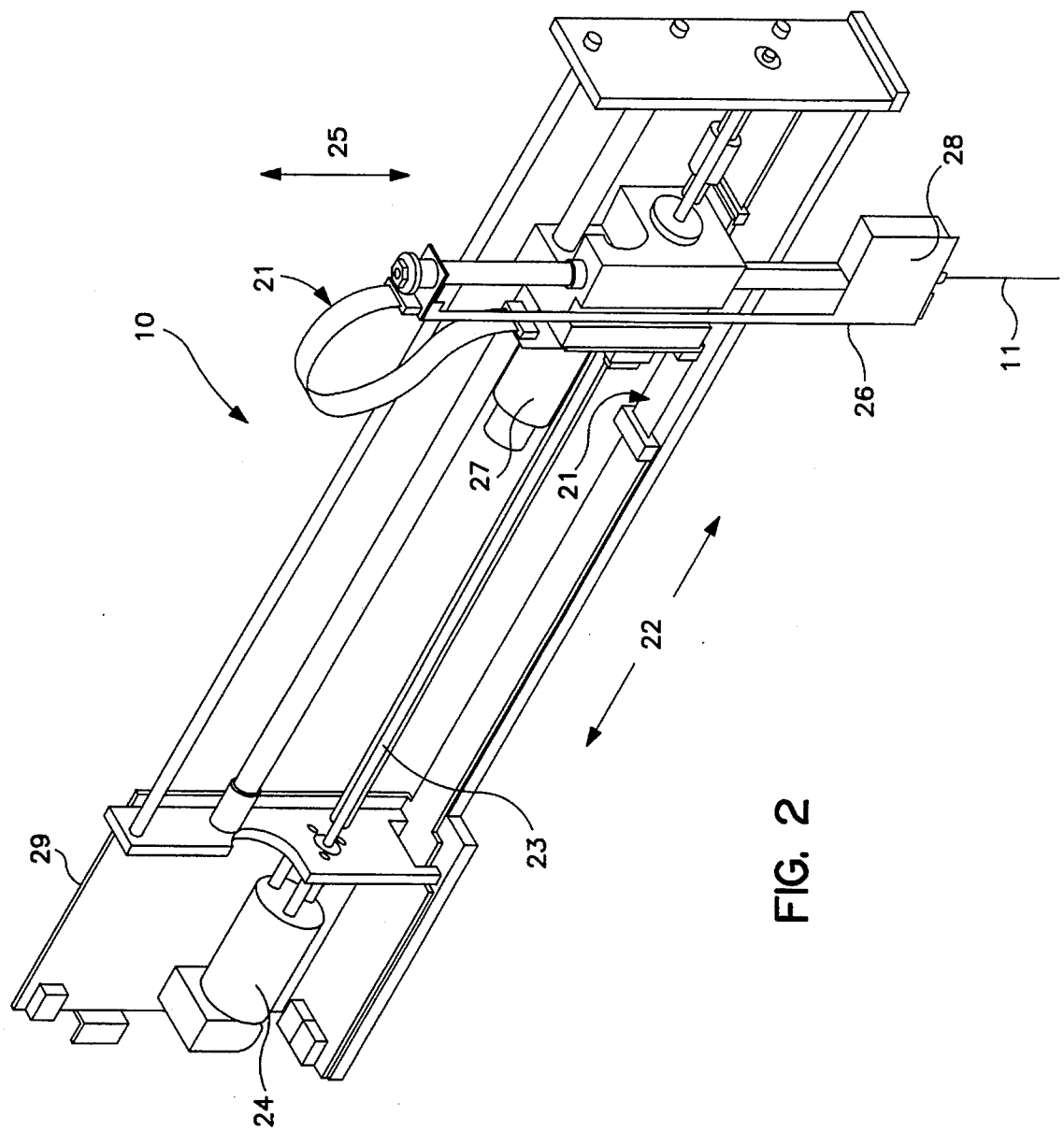
FIG. 2 is a perspective view of a robotic arm including a probe and a liquid level sensor control circuit according to the present invention.

FIG. 2 is a perspective view generally showing a preferred embodiment of robotic arm 10 including a probe 11 and a liquid level sensor control circuit according to the present invention. Probe 11 can be a sampling probe or a piercing and sampling probe for piercing rubber caps used to seal medical sample collection tubes, such as that disclosed in the previously mentioned application to Moreno. When probe 11 is a piercing sampling probe, it is preferably sharpened in accordance with the piercing probe disclosed in the previously mentioned application to Moreno. Moreover, when probe 11 is a piercing sampling probe, it is adapted for detecting the surface of a liquid in a container when piercing the cap of the container. Probe 11 senses a liquid-air interface of a conductive liquid in container 13, such as blood or plasma, while probe 11 moves into container 13 for accurately positioning probe 11 with respect to the surface of the liquid.

Probe 11 is controllably moved along a horizontal axis 22 by lead screw 23 driven by horizontal lead screw motor 24. Vertical movement for raising and lowering probe 11 along axis 25 is provided by gear rack 26 driven by vertical motor 27 and a pinion assembly (not shown). Motors 24 and 27 are each selectively controlled by signals received from associated motor controllers, which are part of the liquid level sensor control circuit of the present invention. Motor controller 32, for example, is shown in the schematic block diagram of FIG. 3. Motor 27 provides sufficient torque for driving probe 11 through a septum of a sealed container when probe 11 is a piercing probe.

Figure 3:
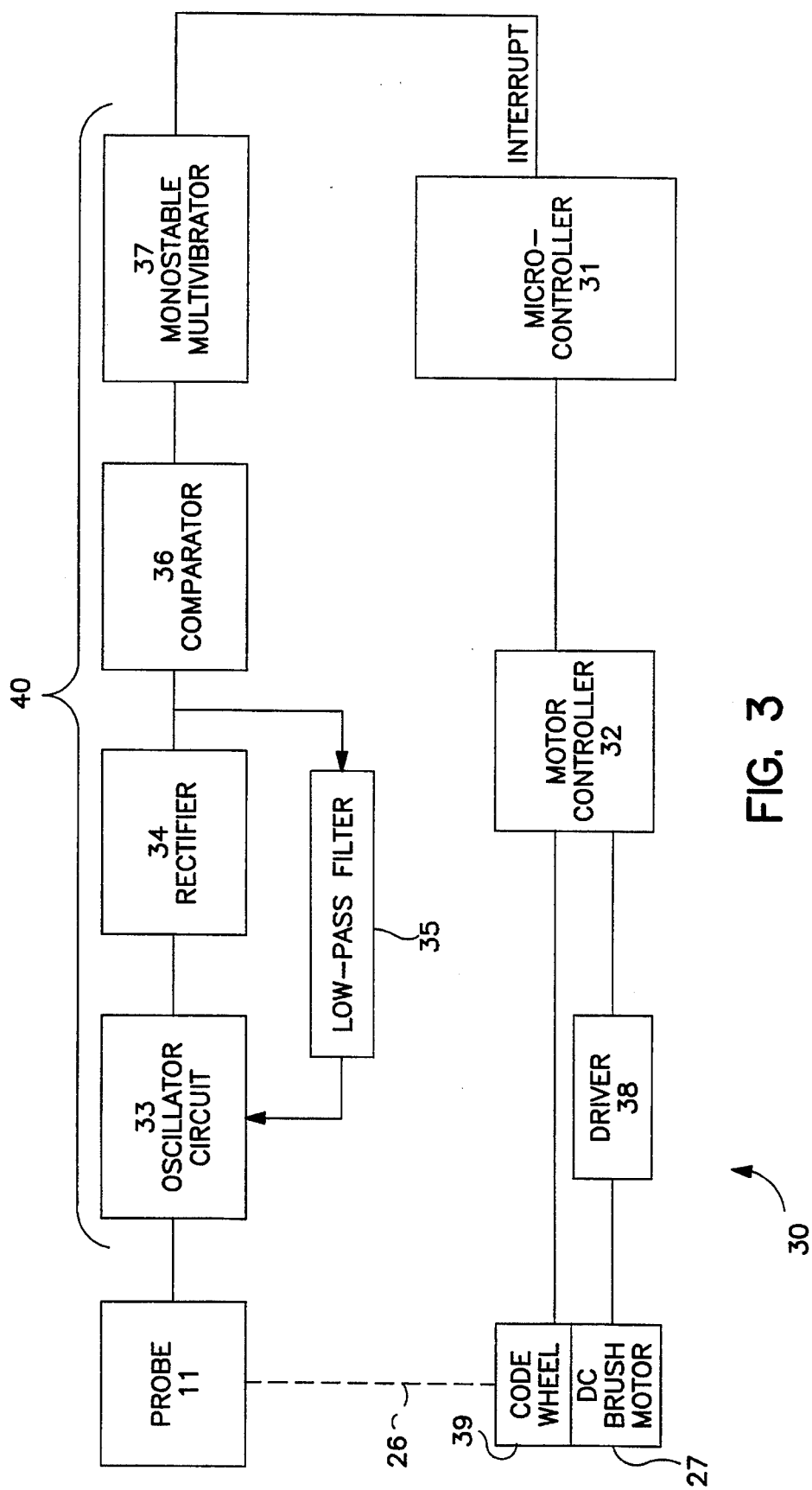
FIG. 3 is a schematic block diagram of a liquid level sensor control circuit according to the present invention.
Figure 4:
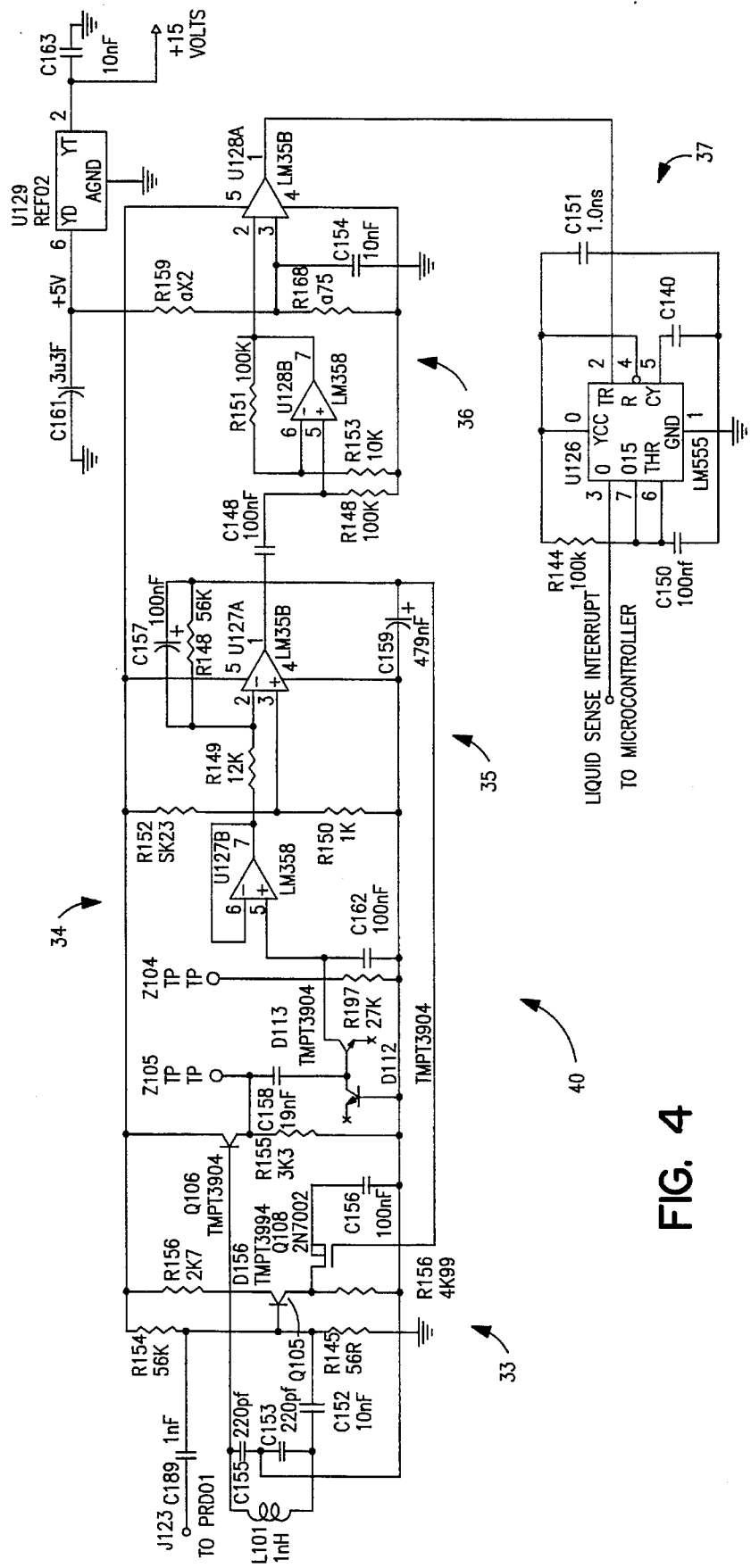
FIG. 4 is a schematic diagram of a liquid level sensor control circuit according to the present invention.

Liquid level sensor control circuitry 30, shown in FIGS. 3 and 4, is coupled to probe 11 for sensing a liquid-air interface. One portion of liquid level sensor control circuitry 30 is located on a printed circuit board mounted to a rack assembly holding probe 11 at 28. Another portion of circuitry 30 is located on a printed circuit board mounted at 29. Of course, the liquid level sensor control circuitry according to the present invention can be located together on a single printed circuit board.

Microcontroller 31 is a two-axis arm controller, that is, microcontroller 31 and the two motor controllers monitor and control the horizontal position of the rack assembly holding probe 11 and the vertical position of probe 11 with respect to the surface of a liquid. Microcontroller 31 and motor controller 32 correlate the position of probe 11 with signals received from liquid sensor circuit 40 (FIGS. 3 and 4) for determining the height of the liquid within a container. Flex cables 21 couple electrical signals between various portions of the control system according to the present invention. As previously mentioned, probe 11 can also be fitted with a heating coil for preheating sampled fluids prior to dispensing into a reaction chamber.

FIG. 3 is a schematic block diagram of a liquid level sensor control circuit 30 having a liquid sensor circuit 40 according to the present invention. Probe 11 is coupled to constant frequency oscillator circuit 33. The constant frequency output of oscillator circuit 33 is coupled to rectifier circuit 34 for generating a rectified output of the oscillator. The output of rectifier circuit 34 is coupled to low-pass filter 35 and fed back to oscillator for controlling an amplitude level of the oscillator. Comparator 36 is also coupled to the output of rectifier circuit 34 for detecting amplitude changes in the rectified output of oscillator circuit 33. The output of comparator 36 is coupled to monostable multivibrator 37 for generating an interrupt pulse when an amplitude change has been detected.

The interrupt pulse indicates that probe 11 has contacted the surface of a liquid and the control circuit responds by determining how much farther probe 11 can be lowered past the surface of the liquid for aspirating a predetermined amount of liquid to be analyzed. Microcontroller 31 provides control signals to motor controller 32 for controlling the position of probe 11. Motor controller 32 responds to the control signals output from microcontroller 31 by outputting appropriate drive signals to driver 38. Motor 27 is responsive to output signals from driver 38 for vertically driving probe 11. A code wheel 39 associated with motor 27 outputs signals to motor controller 32 for monitoring vertical positioning of probe 11.

FIG. 4 is a schematic diagram showing details of the liquid sensor circuit 40 according to the present invention. Oscillator circuit 33 is configured as a Colpitts oscillator including a tank circuit formed by L101, C153 and C155 for oscillating at a constant frequency. The tank circuit is capacitively coupled to probe 11. Probe 11 is a single electrode input to liquid sensor circuit 40 and is capacitively coupled to the tank circuit of oscillator circuit 33. When probe 11 contacts a conductive material, in the present situation, a liquid, the capacitance increase between the probe and the ground plane formed by chassis 18 of the automated blood/plasma sampling system causes the amplitude of the constant frequency oscillator output to decrease slightly. This amplitude change is detected and is used for triggering a monostable multivibrator whose output activates an interrupt to microcontroller 31.

Referring to FIG. 4, oscillator circuit 33 includes transistors Q105 and Q106 configured as a Colpitts oscillator and an emitter follower, respectively. Of course, oscillator 33 can be configured as other well-known oscillator circuits, such as a Pierce or a Hartley oscillator circuit configuration, as long as the gain of the oscillator can be controllably adjusted. The tank circuit of the Colpitts oscillator is formed by L101, C153 and C155 having a constant resonance frequency given by $$f = \frac{1}{2\pi((L101 \cdot C153 \cdot C155)/(C153 + C155))^{1/2}} \approx 480 \text{ KHz}$$

This particular frequency provides optimal sensitivity for capacitive liquid sensing using standard component values, that is, a maximum response from liquid sensor circuit 40 for a given smallest volume of liquid. Other frequencies, for example, between 400 KHz to 1 MHz, could also be used depending on the available space for components of liquid sensor circuit 40. The signal available at the collector of Q105 is coupled to L101 and C155 to provide positive feedback for the oscillator. Resistors R154 and R145 coupled between +5 V and ground set the bias level of the base of transistor Q105. Resistor R156, coupled between a +5 V power supply and the collector of Q105, and R158, coupled between the emitter of Q105 and ground, set biasing levels for the collector and emitter of transistor Q105, respectively. Emitter resistor R158 also limits AC gain of the oscillator. Transistor Q105 can be any suitable transistor such as, for example, a THPT3904.

The drain of MOSFET transistor Q108 is coupled to the emitter of Q105, while the source of transistor Q108 is coupled to ground through capacitor C156. Transistor Q108 operates to increase AC gain of the oscillator as the voltage applied to the gate of transistor Q108 increases by bypassing the AC signal through C156. When the product of the feedback network gain and open loop gain of the amplifier exceeds unity, the circuit 53 will oscillate. Transistor Q108 can be any suitable transistor such as, for example, a 2N7002.

Transistor Q106 is configured as an emitter follower for buffering the oscillator output. The base of transistor Q106 is coupled to the collector of transistor Q105. The collector of transistor Q106 is coupled to the +5 V power supply, while the emitter is coupled to ground through emitter resistor R155. Node Z105 is coupled to the emitter of transistor Q106. At steady state, the AC signal level at node Z105 is approximately 1.6 V peak-to-peak.

Rectifier circuit 34 includes capacitor C158, diodes D112 and D113, buffer U127B and amplifier U127A. Capacitor C158 couples the oscillator signal from the emitter of transistor Q106 to diodes D112 and D113. Diodes D112 and D113 are each transistors, such as a THPT3904, configured as diodes for halfwave rectifying the AC voltage coupled through capacitor C158. Of course, diodes could be used in place of transistors for D112 and D113, as well as a fullwave rectifier circuit configuration. Resistor R157 and capacitor C162 are connected to diodes D112 and D113 for filtering the halfwave rectified signal to provide a DC level of approximately 350 mV at node Z104. Buffer U127B buffers, the rectified output. As shown, buffer U127B is a operational amplifier, such as an LM356, configured for unity gain, however, any unity gain circuitry arrangement could be used, for example, a dedicated integrated circuit buffer or a transistor configured as an emitter follower, if the output will swing to at least 3.7 Volts with a capacitive load.

The output of buffer U127B is coupled through resistor R149 to the inverting input of amplifier U127A. Amplifier U127A can be formed from an integrated circuit operational amplifier, such as an LM356, or can be formed from discrete components such that a gain-bandwidth product and DC offset performance sufficient for present purposes is provided. The output of amplifier U127A is coupled back to the inverting input through the parallel combination of resistor R146 and C157 providing negative feedback so that output of buffer U127B is amplified by about −5.6. Resistors R152 and R150 are coupled between +5 V and ground for producing a reference voltage of about 800 mV. This reference voltage is coupled to the non-inverting input of amplifier U127A and is amplified by about 6.6. In other words, the buffered output voltage from U127B is compared to the 800 mV reference level and the difference is amplified. Consequently, as the rectified output of oscillator 33 decreases, the output of U127A increases.

The output of amplifier U127A is filtered by low-pass filter 35, R147 and C159, and coupled to the gate of MOSFET transistor Q108. As the filtered voltage applied to the gate of transistor Q108 increases, the AC gain of the oscillator increases until the AC signal returns to its nominal steady state level. That is, the conductance of transistor Q108 increases with an increasing output of low-pass filter 35 shunting AC signal at the emitter of Q105 to ground and increasing the loop gain of the Colpitts oscillator. The output of low-pass filter 35 acts to servo the oscillator output to a fixed level, adjusting for changes in the electrical impedance at the probe input caused by mechanical variations of the probe and rack system, and/or presence of the optional probe heater.

The RC time constants in the servo loop produced by R147 and C159 of low-pass filter 35, and R146 and C157 in the feedback loop of amplifier U127A cause the output of U127A to include transients caused when probe 11 touches a conductive material and changes the constant oscillation frequency of oscillator circuit 33. These amplitude transients are coupled to comparator 36.

Comparator 36 includes capacitor C148, amplifier U128B, and amplifier U128A configured as a comparator. The amplitude transients are AC-coupled to amplifier U128B through C148 where they are amplified, for example, by about 11, and coupled to the inverting input of amplifier U128A. Resistor divider network R159 and R160 produce a reference voltage of about 275 mV which is coupled to the non-inverting input of amplifier U128A. When the output of amplifier U128B is greater than the reference level of 275 mV, the output of amplifier U128A, configured as a comparator, goes low, triggering monostable multivibrator 37.

Multivibrator 37 is formed by, for example, an LM555, configured to produce a 10 ms pulse output which is coupled to an interrupt input of microcontroller 31, signalling that the surface of a liquid has been sensed. Of course, any multivibrator circuit responsive to the output of amplifier U128A, whether formed by an integrated circuit or from discrete components, which produces a suitable pulse can be used for multivibrator 37.

The +5 V power supply for liquid sensor circuit 40 is derived from a +15 V supply which is also used to power the optional probe heater. Voltage reference U129 provides a stable +5 V supply for isolating liquid sensor circuit 40 from electrical noise generated by digital circuits of the automated blood/plasma sampling system and appearing on the +15 V supply which may cause false liquid/air interface interrupt signals. Voltage reference U129 also isolates liquid sensor circuit 40 from electrical noise generated on the +15 V supply caused by intermittent connection of the probe heater to the +15 V supply when the probe heater circuitry is active. To further avoid false interrupt signals, the probe heater is momentarily disabled by microcontroller 31 when a "move to liquid" command is executed. After a liquid-air interface is sensed, or when a maximum seek distance of probe 11 is achieved, the heater is enabled.

Liquid sensor circuit 40 can also be used to find the home position of the probe assembly. A grounded spring-loaded pin is mounted at the upper end of travel of the probe assembly. When a post on the probe assembly contacts this pin, the amplitude of oscillator 33 decreases causing liquid sensor circuit 40 to generate an interrupt pulse.

Liquid sensor circuit 40 is preferably manufactured using surface mount technology to provide a small assembly for mounting at 28 in FIG. 2 on the rack assembly holding probe 11. However, the entire control circuit according to the present invention, or a portion of it, may be fabricated using surface mount technology or, for that matter, be an application specific integrated circuit (ASIC).

While there have been described what are presently believed to be the preferred embodiment of the invention, it will be apparent to one skilled in the art that numerous changes can be made in the structure, proportions and conditions set forth in the foregoing embodiments without departing from the invention as described herein and as defined in the appended claims.

What is claimed is:

1. A liquid level sensor circuit for sensing a surface of a liquid in a container, comprising:

a probe for touching the surface of the liquid in the container;

an oscillator circuit coupled to the probe for producing a first output signal having an amplitude and a constant frequency, a filter means being in communication with said oscillator circuit to servo the oscillator output signal to a fixed level by controlling the amplitude of the first output signal, an amplitude of the first output signal changing in response to a capacitance change when the probe touches the surface of the liquid; and a comparator coupled to the oscillator circuit for comparing the amplitude of the first output signal to a first reference amplitude and for producing a change signal when the amplitude of the first output signal changes with respect to the reference amplitude, the change signal indicating that the surface of the liquid has been detected by the probe.

2. A liquid level sensor circuit according to claim 1, further comprising a rectifier coupled to the first output signal for producing a rectified output signal related to the first output signal, the comparator comparing an amplitude of the rectified output signal to the first reference amplitude for producing the change signal.

3. A liquid level sensor circuit according to claim 1, wherein the probe is a sampling probe and includes a heater for heating sampled liquids contained with the probe.

4. A liquid level sensor circuit according to claim 1, wherein the oscillator circuit and the comparator are attached to a rack assembly holding the probe.

5. The liquid level sensor circuit according to claim 1, further comprising a controller responsive to the change signal for controlling a position of the probe with respect to the surface of the liquid.

6. A liquid level sensor circuit according to claim 5, wherein the probe is a piercing sampling probe for piercing a seal of a sealed container and sampling a liquid in the sealed container, and the controller is responsive to the change signal for controlling the position of the probe with respect to a surface of the liquid in the sealed container.

7. The liquid level sensor circuit of claim 1, wherein said filter is a low pass filter.

8. A liquid level sensor circuit for sensing a position of a probe with respect to a surface of a liquid, comprising:

an oscillator coupled to the probe for generating a constant frequency output signal having a first amplitude when the probe is not touching the surface of the liquid, and having a second amplitude different from the first amplitude in response to a capacitance change when the probe touches the surface of the liquid;

rectifier means coupled to the oscillator for producing a rectified output of the constant frequency output signal;

a filter coupled between the rectifier means and the oscillator to servo the oscillator output signal to a fixed level by controlling the first amplitude of the output signal;

detector means coupled to the rectifier means for detecting when the amplitude of the constant frequency signal changes from the first amplitude to the second amplitude and generating a change signal in response indicating that the surface of the liquid has been detected.

9. A liquid level sensor circuit according to claim 8 further comprising a gain control circuit coupled to the output of the rectifier for controlling a gain of the oscillator.

10. A liquid level sensor circuit according to claim 8, wherein the probe is a sampling probe and includes a heater for heating a sampled liquid contained with the probe.

11. A liquid level sensor circuit according to claim 8, wherein the rectifier includes an amplifier for amplifying the rectified output of the constant frequency output signal.

12. A liquid level sensor circuit according to claim 8, wherein the oscillator, the rectifier means, the filter and the detector means are attached to a rack assembly holding the sampling probe.

13. The liquid level sensor circuit according to claim 8, further comprising controller means responsive to the change signal for controlling a position of the probe with respect to the surface of the liquid.

14. A liquid level sensor circuit according to claim 13, wherein the probe is a piercing sampling probe for piercing a seal of a sealed container and sampling a liquid in the sealed container and the controller means is responsive to the change signal for controlling the position of the sampling probe with respect to a surface of the liquid in the sealed container.

15. The liquid level sensor circuit of claim 8, wherein said filter is a low pass filter.

16. A method for detecting a probe touching a surface of a liquid comprising the steps of:

generating with an oscillator a constant frequency oscillation signal having a first amplitude when the probe does not touch the surface of the liquid and changing to a second amplitude in response to a capacitance change when the probe touches the surface of the liquid;

filtering the oscillation signal by means of a filter coupled to the oscillator to servo the oscillation signal to a fixed level by controlling the first amplitude of the oscillation signal;

rectifying the output of the filtered constant frequency output signal with a rectifier coupled to the filter, the rectified output having a third amplitude when the amplitude of the constant frequency signal is the first amplitude and a fourth amplitude when the amplitude of the constant frequency signal is the second amplitude;

detecting when the amplitude of the rectified output of the constant frequency signal changes from the third amplitude to the fourth amplitude; and generating a change signal in response to detecting a change from the third amplitude to the fourth amplitude indicating that the probe is touching the surface of the liquid.

17. A method for detecting a probe touching a surface of a liquid according to claim 16 further comprising the step controlling a position of the probe with respect to the surface of the liquid in response to the change signal.

18. A method for detecting a probe touching a surface of a liquid according to claim 17, wherein the probe is a piercing sampling probe for sampling a liquid in a sealed container, the method further comprising controlling the position of the probe with respect to a surface of the liquid in the sealed container.

19. A method for detecting a probe touching a surface of a liquid according to claim 16, further comprising the step of adjusting the second amplitude of the constant frequency signal back to the first amplitude when detecting the amplitude of the rectified output of the constant frequency signal changes from the third amplitude to the fourth amplitude.

* * * * *